(12) United States Patent
Butler et al.

(10) Patent No.: US 7,169,960 B2
(45) Date of Patent: Jan. 30, 2007

(54) DEHYDROGENATION PROCESS

(75) Inventors: James R. Butler, Friendswood, TX (US); Gary Reed, Gibsonia, PA (US)

(73) Assignee: Fina Technology, Inc., Houston, TX (US)

( * ) Notice: Subject to any disclaimer, the term of this patent is extended or adjusted under 35 U.S.C. 154(b) by 140 days.

(21) Appl. No.: 11/020,978

(22) Filed: Dec. 22, 2004

(65) Prior Publication Data
US 2006/0135831 A1   Jun. 22, 2006

(51) Int. Cl.
*C07C 5/367* (2006.01)
*B01J 10/00* (2006.01)
*B01J 8/04* (2006.01)

(52) U.S. Cl. .................. 585/440; 585/444; 585/445; 585/443; 585/921; 585/922; 585/923; 585/924; 422/228; 422/205; 422/229; 422/197

(58) Field of Classification Search ............... 585/440, 585/444, 445, 443, 921, 922, 923, 924; 422/228, 422/205, 229, 197
See application file for complete search history.

(56) References Cited

U.S. PATENT DOCUMENTS

| | | | |
|---|---|---|---|
| 4,287,375 A | 9/1981 | Moller et al. | |
| 4,549,032 A | 10/1985 | Moeller et al. | |
| 5,358,698 A | 10/1994 | Butler et al. | |
| 6,096,937 A | 8/2000 | Butler et al. | |
| 6,380,449 B1 | 4/2002 | Butler et al. | |
| 6,713,658 B1 | 3/2004 | Dath et al. | |
| 6,727,398 B2 | 4/2004 | Merrill | |
| 6,781,024 B2 | 8/2004 | Butler et al. | |

*Primary Examiner*—Thuan Dinh Dang
(74) *Attorney, Agent, or Firm*—Shirley A. Kopecky

(57) ABSTRACT

A process for the dehydrogenation of a $C_2$ or $C_3$ alkyl aromatic compound to a corresponding vinyl aromatic compound in a tubular reactor incorporating a spiral flow path. Preferred embodiments of the invention provide processes for the production of styrene or divinylbenzene by the catalytic dehydrogenation of ethylbenzene or diethylbenzene, respectively. A feedstock containing a $C_2$ or $C_3$ alkyl aromatic and steam is supplied into the inlet of a tubular reactor containing a dehydrogenation catalyst and comprising a hydrogen permeable outer wall. The alkyl aromatic compound is dehydrogenated to a corresponding vinyl aromatic compound with the attendant production of hydrogen. The feedstock and products of the dehydrogenation reactor are flowed along a longitudinal spiral flow path providing for an outward radial flow of hydrogen to provide a pressure gradient through the hydrogen permeable outer wall of the reactor with the flow of hydrogen therethrough. Hydrogen is removed from the outer wall of the reactor. The resulting vinyl aromatic product is recovered from the tubular reactor.

18 Claims, 4 Drawing Sheets

DEHYDROGENATION PROCESS

FIELD OF THE INVENTION

This invention relates to the dehydrogenation of $C_2$–$C_3$ alkyl aromatic compounds to produce vinyl aromatics and, more particularly, to the catalytic dehydrogenation of such alkyl aromatic compounds in a tubular reactor incorporating an elongated spiral mixing section and having a hydrogen permeable outer wall.

BACKGROUND OF THE INVENTION

Various vinyl aromatic compounds can be prepared by the catalytic dehydrogenation of corresponding $C_2$ or $C_3$ alkyl aromatic compounds. Such reactions include the catalytic dehydration of monoalkyl or polyalkyl aromatics, such as ethylbenzene and diethylbenzene or the dehydrogenation of alkyl substituted polynuclear aromatic compounds, such as ethylnaphthalene. Perhaps the mostly widely used dehydrogenation process involves the dehydrogenation of ethylbenzene with the production of styrene. The catalytic dehydrogenation of ethylbenzene is typically carried out at temperatures within the range of about 540–660° C. under near atmospheric or even subatmospheric pressure conditions. Typically, an ethylbenzene-steam feed having a steam to ethylbenzene mole ratio of perhaps 7 or 8 or even higher is passed over a dehydrogenation catalyst such as iron oxide in an adiabatic dehydrogenation reactor. The dehydrogenation reactor may be of various configurations including a radial flow reactor such as disclosed in U.S. Pat. No. 5,358,698 to Butler et al. or a linear or tubular reactor such as disclosed in U.S. Pat. No. 4,287,375 and U.S. Pat. No. 4,549,032, both to Moeller et al. As disclosed, for example in the aforementioned '032 patent to Moeller et al., an iron-oxide-based dehydrogenation catalyst is employed in a tubular reactor containing a plurality of reaction tubes which are heated by a hot molten salt bath.

Yet another reactor system for the catalytic dehydrogenation of ethylbenzene to produce styrene is disclosed in U.S. Pat. No. 6,096,937 to Butler et al. In the Butler et al. system, a reactor system comprises a furnace structure which incorporates a plurality of internal reactor tubes which contain a dehydrogenation catalyst and which operate in an ascending heat mode. Here, the reactor system incorporates gas-fired heaters which heat the interior of the furnace to a temperature suitable for dehydrogenation to bring the temperature within the reactor tubes to the desired level by the application of heat which varies along the length of the tubes.

Analogous dehydrogenation reactions can be carried out employing $C_3$ alkyl aromatic compounds. Thus, n-propyl benzene can be dehydrogenated to produce beta methyl styrene, and cumene can be dehydrogenated to produce alpha methyl styrene. Other reactions include the dehydrogenation of ethyl toluene to produce vinyl toluene and the dehydrogenation of diethylbenzene to produce divinylbenzene.

SUMMARY OF THE INVENTION

In accordance with the present invention, there is provided a process for the dehydrogenation of a $C_2$ or $C_3$ alkyl aromatic compound to a corresponding vinyl aromatic compound in a tubular reactor incorporating a spiral flow path. Preferred embodiments of the invention provide processes for the production of styrene or divinylbenzene by the catalytic dehydrogenation of ethylbenzene or diethylbenzene, respectively. In carrying out this embodiment of the invention, a feedstock containing a $C_2$ or $C_3$ alkyl aromatic and steam is supplied into the inlet of a tubular reactor containing a dehydrogenation catalyst and comprising a hydrogen permeable outer wall. The tubular reactor is operated under temperature conditions effective to cause the dehydrogenation of the alkyl aromatic compound to a corresponding vinyl aromatic compound with the attendant production of hydrogen in the presence of the dehydrogenation catalyst. Within the reactor, the feedstock and products of the dehydrogenation reaction are flowed along a spiral flow path extending longitudinally of the reactor and providing for an outward radial flow of hydrogen to provide a pressure gradient through the hydrogen permeable outer wall of the reactor with the attendant flow of hydrogen through the outer permeable wall. Hydrogen is removed from the outer wall of the tubular reactor to enhance the flow of hydrogen through the hydrogen permeable outer wall from the interior to the exterior of the reactor. The resulting vinyl aromatic product is recovered from a downstream or outlet section of the tubular reactor.

In one embodiment of the invention, the hydrogen is removed from the outer surface of the tubular reactor wall by the oxidation of hydrogen flowing through the permeable outer wall to produce water. In another embodiment of the invention, the hydrogen is removed from the outer surface of the tubular wall by flowing an inert gas along the exterior surface of the tubular reactor to carry hydrogen away from the outer surface of the hydrogen permeable wall forming the tubular reactor.

In a further aspect of the invention, a feedstock containing a $C_2$ or $C_3$ alkyl aromatic and steam is supplied into a plurality of tubular reactors located within the interior of a dehydrogenation reactor vessel. The tubular reactors characterized by a hydrogen permeable outer wall are arranged in a parallel relationship relative to one another in which the tubular reactors are spaced laterally from one another and are spaced from the interior wall of the reaction vessel. The tubular reactors each have a mixing stage comprising a longitudinally-extending helical baffle providing a spiral flow path for mixing of the alkyl aromatic compound and steam within the reactor. The interior of the reaction vessel is heated by a gas-fired or other suitable heating system in order to provide a heating zone externally of the tubular reactor to provide an amount of heat which varies along the lengths of the tubular reactors. The supplied mixture of the alkyl aromatic compound and steam flows through the parallel tubular reactors into contact with a particulate dehydrogenation catalyst in the reactor under temperature conditions, resulting from the externally-applied heat, which are effective to cause the dehydrogenation of the alkyl aromatic compound to the corresponding vinyl aromatic in the presence of the dehydrogenation catalyst. Subsequent to the dehydrogenation reaction, the vinyl aromatic product is recovered from the tubular reactors through outlets located downstream of the dehydrogenation catalyst.

In a further aspect of the invention, there is provided a reaction system for the catalytic reaction of a plurality of reactants in a feed stream. The reaction system comprises a plurality of parallel, elongated, tubular reactors having hydrogen permeable walls and provided with inlet and outlet sides. An inlet manifold is connected to the tubular reactors in order to supply a mixture of reactants to the inlet sides of the tubular reactors. The reactors incorporate a mixing section adjacent the inlet sides thereof each reactor comprising at least one static baffle in an elongated helical configuration comprising a spiral flow path. A reaction and products section in each of the tubular reactors is located downstream of the initial mixing section and comprises a bed of catalyst particles and has a helical baffle providing a spiral flow path for the outward radial flow of reaction products. An outlet manifold is connected to the outlet side of the tubular reactors and is effective to supply reaction product from the tubular reactors to a suitable recovery system.

DETAILED DESCRIPTION OF THE INVENTION

Figure 1:
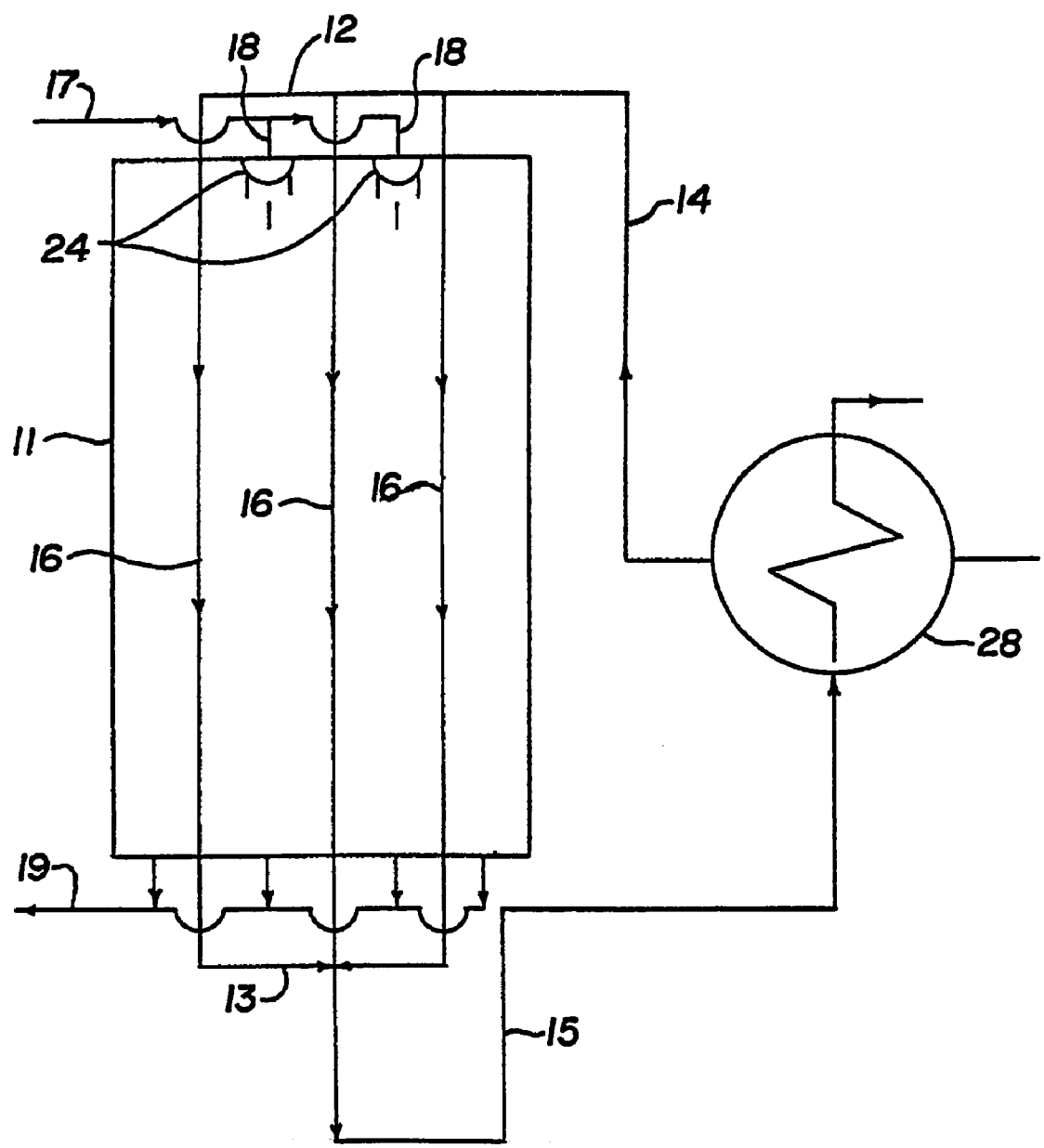
FIG. 1 is a schematic illustration of a reactor incorporating a plurality of tubular reactors for use in carrying out the present invention.

The present invention may be carried out employing tubular reactors of any suitable configuration which incorporates a spiral flow path in conjunction with a semipermeable wall structure. Preferably, however, the invention will be carried out employing tubular reactors employed within a electrically-heated or gas-fired furnace operated in a variable heat mode such as disclosed in U.S. Pat. No. 6,096,937 to Butler et al., and the invention will be described with reference to this reactor configuration. Thus, the reactor may be operated as an ascending heat reactor, as disclosed in the aforementioned '937 patent to Butler et al., or it may be operated as a relatively constant heat adiabatic reactor. Regardless of the nature of the operation of the system, the reactor tubes will incorporate a hydrogen permeable wall section and a helical spiral flow section imparting an outwardly radial flow vector to the reactants, specifically hydrogen, toward the permeable wall section as described in greater detail below.

The feedstock employed in carrying out the present invention is a $C_2$ or a $C_3$ alkyl aromatic compound which can be dehydrogenated to the corresponding vinylaromatic compound. Suitable dehydrogenation processes to which the present invention may be applied include the dehydrogenation of ethylbenzene to produce styrene, the dehydrogenation of n-propylbenzene to produce beta methyl styrene, the dehydrogenation of cumene to produce alpha methyl styrene, the dehydrogenation of ethyl toluene to produce vinyl toluene, the dehydrogenation of a diethylbenzene to produce divinylbenzene and the dealkylation of polynuclear alkyl aromatics, such as the dehydrogenation of ethyl naphthalene to produce vinyl naphthalene. The present invention will be described initially with reference to the dehydrogenation of diethylbenzene to produce divinylbenzene. However, it will be understood that the description of this particular process is fully applicable to other dehydrogenation processes such as described above, in which one of the products is molecular hydrogen which is forced by the radial vector of a spiral flow path against the inner surface of a semipermeable membrane forming the tubular wall structure of the reactor employed in the present invention.

The hydrogen permeable membranes employed in the tubular wall structure of the present invention may be formed of any material which exhibits substantial permeability to hydrogen while being substantially impermeable to the larger molecules involved in the dehydrogenation reaction, specifically ethylbenzene and styrene in the case of the dehydrogenation of ethylbenzene. Where steam is supplied to the interior of the reactor along with the ethylbenzene, the membrane wall structure should also be substantially impermeable to water molecules.

Suitable semipermeable membranes for use in the present invention may take the form of palladium tubular membranes of the type disclosed in Abdalla et al., "Catalyst Dehydrogenation of Ethylbenzene to Styrene in Membrane Reactors" *AICHE Journal*, December 1994, Vol. 40, No. 12. However, while semipermeable membranes of the type disclosed in Abdalla may be used in the present invention, the reactor configurations and the flow characteristics employed in the present invention are substantially different from those enclosed in Abdalla et al. In the present invention, the flow pattern of the reactants, and more importantly the products, including the hydrogen product, involved in the present invention have a distinct outwardly radial vector as contrasted with the flow characteristics of the reactants and products in Abdalla which extend longitudinally along the longitudinal dimension of the reactor.

While a single tubular reactor incorporating the spiral flow pattern of the present invention may be used, as practical matter a large number of tubular reactors will be connected in a parallel as described below. Where the hydrogen gas permeating through the semipermeable membranes in the accordance with the present invention is converted by oxidation, the individual reactor tubes may be spaced from one another to provided clearance for oxygen flow around the periphery of each individual reactor. Suitable spacing as described above should also provide for effective heat transfer away from the outer wall surfaces of the individual tubular reactors.

Where a sweep gas configuration is employed, for example, through the injection of nitrogen to remove hydrogen permeating through the wall of the reactor, each reactor tube will normally be configured to provide an outer casing individually surrounding each reactor to provide an annular flow space for the passage of the nitrogen or other inert sweep gas. Alternately, the reactor tubes may be configured in a reactor vessel as described above with the sweep gas passing around the individual tubes in an unrestricted fashion.

Referring initially to FIG. 1, there is shown a schematic illustration of an ascending-heat diethylbenzene reactor which is disclosed as having a reaction chamber defined by an external shell 11 and having an inlet manifold 12 and an outlet manifold 13. A supply line 14 is connected to inlet manifold 12 to supply a diethylbenzene-steam feed stock, and a product flow line 15 containing divinylbenzene and unreacted diethylbenzene and steam is connected to the outlet manifold 13.

The central section of the diethylbenzene reactor includes a reactor vessel 11 inside of which is located a series of reactor flow tubes 16 which are connected in parallel to the inlet manifold 12. The open bore of each tube 16 is exposed to the inlet manifold 12 to allow the diethylbenzene steam feed to enter through line 14 into inlet manifold 12 and to traverse tubes 16 into outlet manifold 13. Although only three reactor tubes are disclosed in this schematic drawing, in actual practice a large multitude of such tubes normally would be provided in the reactor. A plurality of burners 18 are located at the top of the furnace shell. Burner tubes 18 are connected to a source of fuel such a natural gas, hydrogen, or other combustible gas which is provided by means of fuel inlet line 17 communicating with heater elements 18. A combustion products exhaust line 19 communicates through the wall of chamber 11 to carry the products of combustion from the flames of nozzles 24 of the heater elements. A source of oxygen may also be provided by means of a separate oxygen supply line or air supply line which may be connected to burner tubes 18 separately or may be passed through a mixer box prior to entering line 17 where air or oxygen can be mixed with the gaseous fuel.

In a typical operation, a diethylbenzene feedstock (a mixture of diethylbenzene and steam) is provided through inlet line 14 and flows into the reactor tubes 16. The interiors of reactor tubes 16 may be completely or partially filled with a suitable EB dehydrogenation catalyst. Those skilled in the art are aware of suitable dehydrogenation catalysts which can be advantageously utilized in the present invention. The diethylbenzene feedstock flows from inlet header 12 through tubes 16 and across the chosen catalyst where it undergoes dehydrogenation to produce the resulting divinyl product.

Depending upon the hydrogen dissipation mechanism employed to remove hydrogen from the outer surface of the semipermeable membrane wall structure, the heating elements may supply all or a portion of the heat requirements of the process. Where dissipation of the hydrogen flowing through the semipermeable membrane wall structure of the reaction tubes is supplied through the use of an inert sweep gas, all of the heat requirements of the system may be supplied by operation of the heater elements. However, where hydrogen removal from the exterior wall surface of the reactor tubes is accomplished by oxidation of the hydrogen as it flows through the semipermeable wall sections, the heat produced by combustion of the hydrogen may supply a substantial portion or even all of the heat requirements of the process. In this case, while the heater elements will be operated initially during a startup phase of the process, once the dehydrogenation process is underway with combustion of the hydrogen product, operation of the heater elements may be curtailed or even shut down.

Concurrently with supply of the diethylbenzene feedstock, the gaseous mixture of fuel and oxygen source flows through line 17 and into heater nozzles 24. An ignition source is provided upon startup of the reactor and the gas is continuously passed through nozzles 24 and burns as it exits the nozzles. A minor amount of experimentation can determine the particular nozzle sizes to use for obtaining an ascending-heat thermal reactor. Thus, as diethylbenzene enters line 14 and passes through chamber inlet header 12 into reactor tubes 16, it is passed across the dehydrogenation catalyst contained in the reactor tubes 16 and subjected to an increasing level of heat input due to the gaseous fuel being consumed. Although gaseous fuel is desirable, it is, of course, possible to use a liquid fuel, which can be atomized by the oxygen source gas at a point prior to entering line 17. Other conventional nozzle-heater arrangements can be used with different fuel sources. In addition, it is possible that, rather than a chemically-driven heat supply, one could substitute electrical heating elements which vary in heat generation from the input end of the reactor to the output end of the reactor, to obtain the increasing heat supply for the reactor. Thus, one skilled in the art could substitute electrical heating elements for gas-fired heaters 18 with increasing heat output towards the end of the heating elements associated with the output end of the reactor tube 16.

Usually, it will be desirable to use a heat source that is compatible with the refining operations around the dehydrogenation reactor where the most available fuel is usually hydrogen or a compressed natural gas and therefore the description here is defined in terms of a gas-fired heating system. Upon traversing the length of reactor tubes 16 across the catalyst contained therein, a substantial dehydrogenation of the diethylbenzene feed is accomplished, and the product exiting into the outlet header contains substantial divinylbenzene, which is then passed through product flow line 15 to a heat exchanger 28 in indirect heat exchange with the feed stock in inlet line 14. From the heat exchanger, the dehydrogenated product is passed to a system (not shown) for further purification and removal of by-products such as diethylbenzene, ethylbenzene, benzene, toluene, and such hydrogen as remains in the product stream. As previously mentioned, the combustion gases exiting nozzle 24 flow out through gas exhaust conduit 19 in the bottom of the heater box. Thus there is described a reactor for dehydrogenating diethylbenzene into divinylbenzene which is defined as an ascending-heat reactor to provide heat input for the endothermic diethylbenzene dehydrogenation reaction and, furthermore, to provide increasing amounts of heat toward the end of the dehydrogenation reaction as the components being reacted are being used up and the reaction equilibrium tends to shift to the left.

As described in the aforementioned Butler et al. patent, various changes can be made in the described dehydrogenation reactor system. The flow rate in terms of the liquid hourly space velocity (LHSV) through the tubes can be changed by varying the diameter of the reactor tubes along their length. For example, the reactor tubes can be smaller at the inlet end and larger at the outlet end to provide a decreasing LHSV down the length of each reactor tube. For a further description of a suitable reactor system employing an ascending heat mode of operation, reference is made to the aforementioned U.S. Pat. No. 6,096,937 to Butler et al., the entire disclosure of which is incorporated herein by reference.

It is to be recognized that the parallel reactor tube configuration of the type disclosed in the Butler et al. '937 patent can be employed in adiabatic reaction systems of the type more conventionally used in the dehydrogenation of ethylbenzene to produce styrene. In any case, it will be advantageous in carrying out the invention to employ a plurality of parallel tubular reactors with appropriate manifolding at the inlet and outlet sides of the reactors as described, for example, in the '937 patent.

Figure 2:
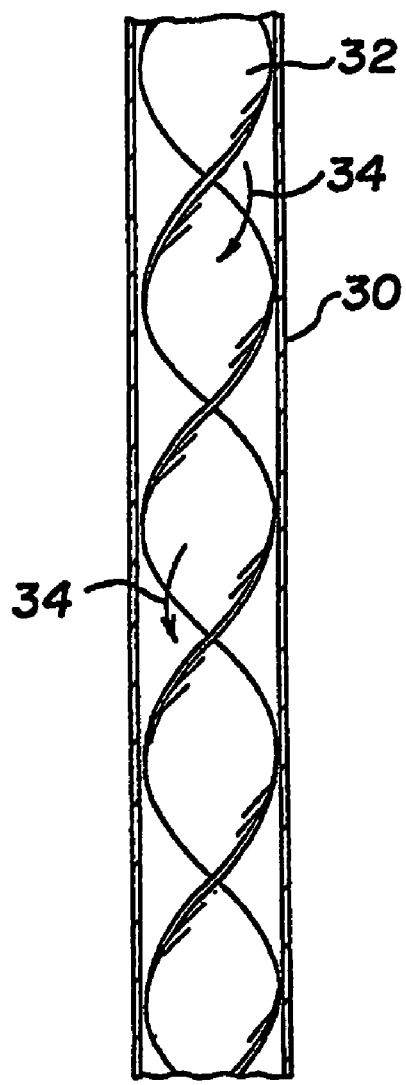
FIG. 2 is a perspective view with parts broken away of a tubular reactor incorporating a helical baffle providing a spiral flow path within the reactor.

Turning now to FIG. 2, there is illustrated a preferred form of a tubular reactor which can be employed in carrying out the invention. FIG. 2 is a perspective view of a cylindrical reactor employing a helical baffle to provide a spiral flow path along the length of the mixer. In FIG. 2, the reactor is shown with one-half of the outer cylindrical shell broken away to reveal the interior of the reactor. As shown in FIG.

2, the reactor incorporates a cylindrical shell 30 formed of a semipermeable membrane with an internal helical baffle 32 providing a spiral flow path for the feedstock-product mixture as indicated by arrows 34. In the embodiment illustrated in FIG. 2, the baffle has a pitch of at least about 30° (from the longitudinal axis at the reactor) to provide for good mixing of the steam and diethylbenzene components along with a substantial radial vector of the flow of the reaction product and to provide for a relatively constant radial temperature gradient. That is, the temperature is relatively constant across the width of the mixer. In many cases, it will be desirable to provide a greater pitch of about 30–50% from the longitudinal axis in order to impart a greater radial vector to force greater amounts of hydrogen from the interior of the tube into contact with the inner surface of the semipermeable membrane of the reactor. This, in conjunction with the removal of the hydrogen from the vicinity of the outer surface of the semipermeable membrane wall, enhances the hydrogen partial pressure gradient from the interior to the exterior of the reactor to facilitate removal of hydrogen from the reaction zone. This, in turn, biases the dehydrogenation reaction to the right.

Figure 3:
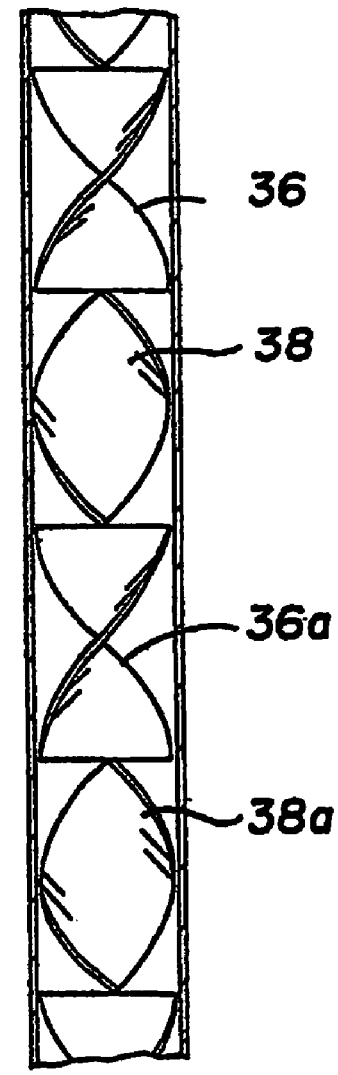
FIG. 3 is a perspective view of a modified form of a reactor incorporating two flights of helical baffles.

While only a single or continuous helical baffle is employed in the reactor of FIG. 2, a further embodiment of the invention involves the use of an inline reactor having a plurality of helical baffle sections. A reactor incorporating this embodiment of the invention is illustrated in FIG. 3, which is a perspective illustration, with parts broken away of a reactor having a first baffle section 36 and at least one second baffle section 38, which is angularly displaced (e.g., by 90° in the embodiment shown), with respect to the first baffle section 36, of a different pitch than the first baffle. This embodiment of the invention may be used where the baffle is incorporated in a portion of the tubular reactor as described below and provides for thorough and efficient mixing of the two components initially after which a generally more linear flow takes place through a portion of the tubular reactor containing a dehydrogenation catalyst followed by flow through a baffle importing a spiral flow path to promote the flow of hydrogen against a semipermeable membrane. As an example of the embodiment illustrated in FIG. 3, baffle section 38 may be followed by baffle section 36*a* (displaced by 90°) followed in turn by baffle section 38*a* again displaced by 90°. In a further embodiment of the invention (not shown) one baffle may have a designated pitch with the other baffle having a different pitch.

Figure 4:
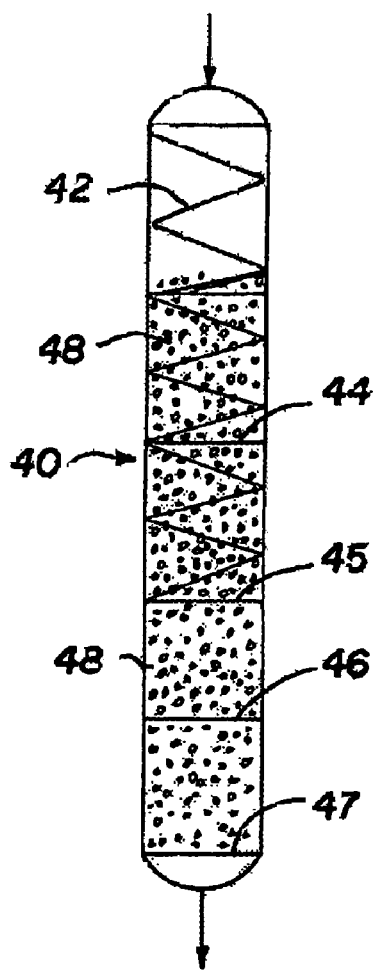
FIG. 4 is a schematic illustration of one form of tubular reactor configured with an initial spiral mixing section.

FIG. 4 is a schematic illustration with parts broken away of a tubular reactor configured with an initial helical flow reaction section with the remainder of the reactor packed with particulate dehydrogenation catalysts. While only a single tubular reactor is illustrated in FIG. 4 and in the following FIGS. 5 and 6, it is to be understood that a commercial dehydrogenation reactor will have a plurality of tubular reactors which are manifolded as described above with respect to the aforementioned '937 patent. For example, a commercial reactor implementing the present invention typically will contain from 30 up to about 1,000 tubular reactors connected in parallel to suitable intake and exhaust manifolding systems. More particularly, and referring to FIG. 4, the tubular reactor contains a spiral baffle 42 which conforms to the single baffle section illustrated in FIG. 2. In addition, the tubular reactor includes perforated grid plates 44, 45, 46, and 47 which support a particulate dehydrogenation catalyst 48 throughout the length of the tubular reactor and extending at least partially into the spiral section 42. Dehydrogenation catalyst 48 may be of any suitable type, typically constituting an iron oxide-based catalyst comprising iron oxide or a mixture of iron oxide with chromium oxide and sodium oxide, as disclosed in the aforementioned U.S. Pat. No. 4,549,032 to Moeller. As illustrated, the top portion of the reactor involving a portion of the length of the baffle is free of catalysts in order to allow a spiral flow path of the reactants initially before contacting the dehydrogenation catalysts. However, the dehydrogenation catalyst may extend further upwardly and be packed in most or even all of the spiral baffle. In any case, the reactor flow configuration should provide for significant radial flow after contact of the reactants with the dehydrogenation catalyst in order to facilitate removal of the hydrogen from the reactor and thus drive the dehydrogenation reaction to the right.

Figure 5:
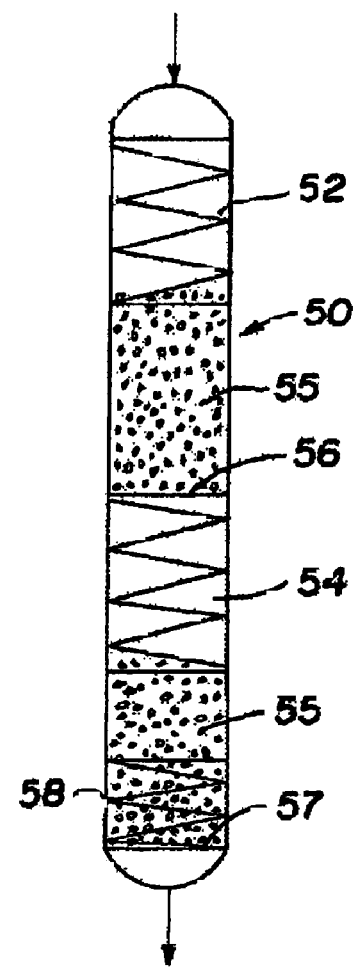
FIG. 5 is a schematic illustration of another embodiment of the invention incorporating several spaced spiral stages.

FIG. 5 illustrates another embodiment of the invention in which a tubular reactor 50 incorporates an initial mixing stage 52 and a second spaced and intermediate spiral baffle 54. Catalyst particles 55 are interposed on suitable grid plates 56 and 57 above and below the intermediate section 54. Sections 52 and 54 may be identical or different and may incorporate a single baffle as disclosed in FIG. 2 or multi-baffle spirals of the type described above with respect to FIG. 3. As before, the catalyst particles extend upwardly into a lower portion of the baffle in the initial mixing section 52. Similarly, the catalyst particles supported on grid 57 extend upwardly, partially into section 54 to encompass at least a lower portion of this section. In Section 54, after the reactants traverse the catalyst bed 55 with the production of hydrogen by the dehydrogenation reaction, the spiral flow in Section 54 directs hydrogen outwardly against the semipermeable membrane, forming the wall structure of the tubular reactor. Alternatively, the particulate dehydrogenation catalyst may extend throughout the lengths of one or both of mixing sections 52 and 54. In Section 55, the lower portion immediately above grid plate 57 is provided with a spiral baffle 58 in order to drive reaction products radially outward against the inner surface of the semipermeable membrane forming the wall structure of the reactor.

Figure 6:
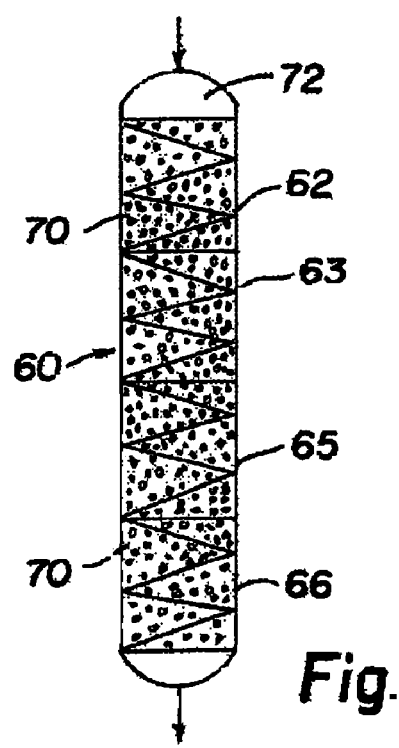
FIG. 6 is a schematic illustration of yet another embodiment of the invention incorporating helical baffles extending throughout a substantial length of tubular reactor.

FIG. 6 illustrates yet another embodiment of the invention in which all or at least a predominant portion of the longitudinal dimension of the tubular reactor incorporates one or more helical baffles providing one or more spiral flow paths throughout the length of the tubular reactor. In this embodiment of the invention, a tubular reactor 60 incorporates a series of spiral baffles 62, 63, 65, and 66, each corresponding to a baffle of the type illustrated in FIG. 2, disposed along the length of the tubular reactor. Each of the sections is packed with a particulate dehydrogenation catalyst 70 with the initial mixer preferably containing catalysts in only a lower portion of the mixing section 62, similarly, as described above with respect to FIG. 4. Alternatively, the catalyst can extend upwardly through most or all of the initial static mixer or even into the plenum area 72 above the mixer 62. In FIG. 6, a spiral flow path is provided throughout substantially the length of the tubular reactor. While in the embodiment illustrated this is provided by a plurality of baffle sections stacked one on top of the other, it will be recognized that a continuous helical baffle can be provided by a single helix extending throughout the length of the tubular reactor.

The present invention, through the use of an inline static mixing section encompassing all or a portion of the tubular reactor, offers significant advantages in terms of selectivity to production of the desired dehydrogenated product and in terms of the possibility of relatively low steam to hydrocarbon mole ratio (SHR).

While, as indicated previously, the present invention can be carried out with other alkyl aromatic feedstocks, principally the dehydrogenation of ethylbenzene to produce styrene, the application of a specific embodiment of this invention in which divinylbenzene is produced involves challenges which must be addressed in order to provide an effective yield with undesirable side effects. Diethylbenzene is encountered in plant operations as a mixture of the ortho, meta, and para isomers in equilibrium conditions in which the meta and para isomers predominate. However, ortho diethylbenzene will often be present, and it is preferred in carrying out the present invention, to provide a feedstock in which the presence of ortho diethylbenzene is kept to a very low level in order to avoid the production of indene as a byproduct. In order to minimize the production of napthalene, the feedstock should, if practical, be made free of ortho diethylbenzene. Preferably, ortho diethylbenzene should be present in a mixture of the three isomers in admixture with the other two isomers in an amount of no more than 10 mole percent, and preferably no more than 5 mole percent, of the ortho isomer. Substantially lower amounts of the ortho isomer, ranging down to 1 mole percent or less such that the feed stream is substantially free of ortho diethylbenzene, should be employed.

In carrying out the present invention, diethylbenzene feedstocks comprising a mixture of the meta and para isomers at a mole ratio within the range of 3:2 to 2:3 may be employed. Usually, the feed stream will contain a mixture of these isomers with the meta isomer being the predominant component to provide a mole ratio of meta diethylbenzene to para diethylbenzene in a mole ratio of about 3:2. However, pure isomer feedstocks may be employed, specifically feedstocks in the nature of highly pure para diethylbenzene with only minor amounts of meta diethylbenzene, and as noted previously, the feed stream being substantially free of ortho diethylbenzene. Alternatively, relatively pure meta diethylbenzene can be employed where the desired product is meta divinyl benzene.

Where the undesirable ortho diethylbenzene is present in a feedstock in any significant amounts, the feedstock comprising a mixture of the three isomers can be supplied to a fractionation column. In the operation of the fractionation column, the ortho diethylbenzene is concentrated in the bottoms product, and the remaining mixture of the other isomers of diethylbenzene are then supplied to the dehydrogenation reactor.

Where a feedstock comprising ethylbenzene for the production of styrene by catalytic dehydrogenation is employed, the process is more straightforward and comparatively simple than where a dialkyl aromatic feedstock, such as diethylbenzene, is employed. However, aside from considerations, such as outlined above, trends observed in the dehydrogenation of ethylbenzene to produce styrene can be applied to the dehydrogenation of diethylbenzene and various other aromatic substrates as described previously.

The present invention can be employed incorporating any suitable dehydrogenation catalyst suitable for the dehydrogenation of the alky aromatic feedstock. Such catalysts normally incorporate iron oxide along with secondary components such as chrome oxide as well as other inorganic materials and are typically formulated with a binder in particle sizes of about ⅛-inch. One suitable catalyst for use in carrying out the present invention is iron oxide catalyst promoted with potassium carbonate plus trace metals for selectivity enhancement available from CRI Catalyst Company under the designation "Flexicat Yellow."

The potassium-promoted iron oxide catalyst described above is especially suitable in the dehydrogenation of diethylbenzene in the production of divinylbenzene, as well as in the dehydrogenation of ethylbenzene to produce styrene. Such catalysts can also be employed in the dehydrogenation of feedstocks involving ethyl naphthalene, cumene, n-propyl benzene, or ethyl toluene as described previously. The reactor configuration can be the same regardless of the nature of the alkyl aromatic compound contained within the feed stream. The reaction conditions will be generally the same, although they may vary somewhat. Normally, the principal variant will be in the steam to hydrocarbon mole ratio. By way of example, the steam to hydrocarbon mole ratio (SHR) will generally be higher for the dehydrogenation of diethylbenzene to produce divinylbenzene than will be the SHR for the production of vinyl toluene. For example, the SHR for these processes may be about 16:1 for the production of divinylbenzene and about 12:1 for the production of vinyl toluene. These are somewhat higher than the SHR for the production of styrene, typically about 6:1. In the dehydrogenation of a polynuclear aromatic, such as ethyl naphthalene, the reactor conditions normally will be similar to those observed for the production of divinylbenzene. Temporary conditions will be about the same for the various feed streams, for example, an inlet temperature of about 620–660° C. and an outlet temperature of about 50–60° C. less than the inlet temperature.

Figure 7:
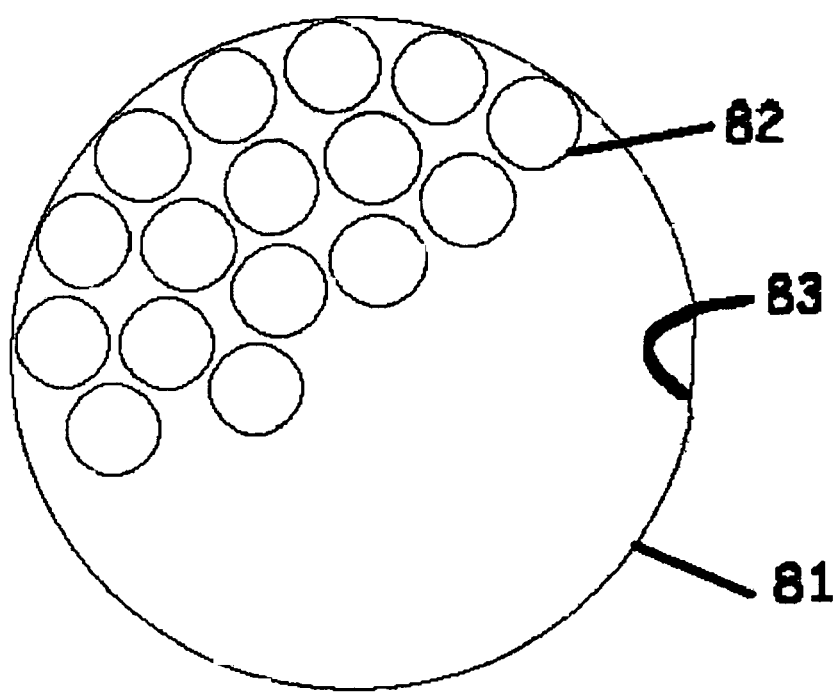
FIG. 7 is a schematic illustration showing a horizontal section through a reactor vessel incorporating a plurality of horizontally spaced tubular reactors for use in carrying out an embodiment of the invention.

As described previously, the combination of the spiral flow of reaction products through a tubular reactor and a semipermeable membrane wall structure of the tubular reactor provides for removal of hydrogen from the reaction zone with an attendant increase in the reaction rate of the dehydrogenation process. As described previously, the invention will normally be carried out with a plurality of tubular reactors arranged in a parallel relationship within a reaction vessel. FIG. 7 illustrates an idealized transverse horizontal sectional view through a reaction vessel 80 illustrating a plurality of tubular reactors 82 spaced interiorly within the reaction vessel in order to provide for the combustion of hydrogen traversing the semipermeable reactor walls or a sweep gas flowing to disperse hydrogen away from the individual reactors. More particularly and as shown in FIG. 7, there is illustrated a reactor vessel 80, analogous to the reactor 11 shown in FIG. 1 within which are dispersed a plurality of tubular reactors 82, analogous to the reactor tubes 16 of FIG. 1, which are spaced from one another and from the wall 83 of the reaction vessel to provide for gas flow about the exterior surfaces of the tubular reactors. The tubular reactors 82 are configured as described previously to provide a spiral flow path within the interiors thereof and incorporating a hydrogen permeable membrane providing the wall structures of the tubular reactors. The reaction vessel 80 is also supplied with the appropriate input and output manifolding (not shown), analogous to that shown in FIG. 1 together with heating elements, analogous to those indicated by reference numeral 18 in FIG. 1, which can function for the supply for an oxygen-fuel mixture initially followed by the injection of an oxygen-containing gas such as air, to provide for the combustion of hydrogen emanating from the walls of the tubular reactors 82. Once a suitable temperature to support combustion is established within the reaction vessel 80, the heat requirements can be supplied solely by the combustion of hydrogen emanating from each reactor tube 82, as described previously.

As indicated in FIG. 7, the reactor tubes are spaced from one another and from the interior wall 83 of reaction vessel 80 in order to provide clearance for oxygen flow around the peripheries of the individual reactors. If desired, an oxidation catalyst may be disposed within the reaction vessel 80 about the outer surfaces of the tubular reactors 82 in order to facilitate oxidation of the hydrogen flowing through the semipermeable wall sections of the tubular reactors. Any suitable oxidation catalyst may be employed in this embodiment of the invention. For example, the oxidation catalyst may take the form of platinum or palladium coatings on the permeable tube.

Figure 8:
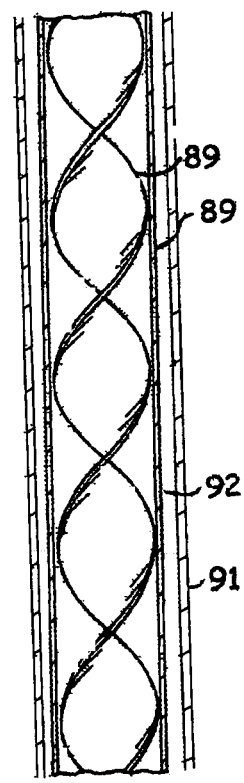
FIG. 8 is perspective view with parts broken away illustrating yet another embodiment of the invention in which a sweep gas can be employed to remove hydrogen from the external reactor surface.

While the reaction vessel configuration of FIG. 8 can be most effectively used for the embodiment of the invention in which hydrogen removal from the outer surfaces of the tubular reactors is effected by oxidation of the hydrogen, this configuration may also be employed where the hydrogen is removed from the outer surfaces of the tubular reactors through the use of an inert sweep gas such as nitrogen flowed through the reaction vessel to reduce the hydrogen concentration in the vicinity of the outer walls of the tubular reactors 82. The flow of sweep gas may be concurrent or countercurrent to the flow of reactants and reaction products within the interiors of the tubular reactors.

In another embodiment of the invention where a sweep gas is employed for the removal of hydrogen, all or part of the tubular reactors within the reaction vessel are provided with an outer casing establishing an annular space surrounding the semipermeable membrane wall structure of the tubular reactor. This embodiment of the invention is illustrated in FIG. 8, which is a side elevational view of a tubular reactor similar to that shown in FIG. 2. The reactor provides a cylindrical wall 88 formed of a semipermeable membrane and an internal helical baffle 89 providing for spiral flow through the reactor. The cylindrical semipermeable membrane 88 is surrounded by a concentric tubular member 91 which is of a larger diameter than the tubular member 88 to provide an annular space 92 between the outer surface of the semipermeable membrane 88 and the inner surface of the tubular member 91. The tubular member 91 is, of course, substantially impermeable to hydrogen or other gases so that the inert sweep gas may be introduced into the annular space 92 to carry hydrogen away from the outer surface of the membrane wall structure 88. The tubular member 91, as well as the interior reactor, is supplied to suitable manifolding (not shown) at the top and bottom of the reaction vessel so that sweep gas may be introduced into and withdrawn from the reaction vessel. The annular space 92 should be of a sufficient capacity to effectively remove hydrogen from the outer surface of the tubular reactor. For example, where the tubular reactor 88 has an outer diameter of about 4 inches, the outer cylindrical member 91 may have an internal diameter of 5 inches to provide for 1 inch clearance between the semipermeable membrane and the cylindrical shell 91.

Having described specific embodiments of the present invention, it will be understood that modifications thereof may be suggested to those skilled in the art, and it is intended to cover all such modifications as fall within the scope of the appended claims.

The invention claimed is:

1. A process for the production of a vinyl aromatic compound by the catalytic dehydrogenation of $C_2$ or $C_3$ alkyl aromatic compound comprising:
   (a) supplying a feedstock containing a $C_2$ or $C_3$ alkyl aromatic compound and steam into an elongated tubular reactor containing a dehydrogenation catalyst and comprising a hydrogen permeable outer wall extending longitudinally of said reactor;
   (b) operating said tubular reactor under temperature conditions effective to cause the dehydrogenalion of said alkyl aromatic compound to a corresponding vinyl aromatic compound with the attendant production of hydrogen in the presence of said dehydrogenation catalyst;
   (c) flowing said feedstock within at least a portion of said reactor along a spiral flow path extending longitudinally of said reactor and providing for an outwardly radial flow of hydrogen to provide a pressure gradient through said hydrogen permeable outer wall with the attendant flow of hydrogen through said permeable outer wall;
   (d) removing hydrogen from the vicinity of the outer wall of said tubular reactor in enhance the flow of hydrogen through said hydrogen permeable outer wall from the interior to the exterior of said reactor; and
   (e) recovering said vinyl aromatic product from a down stream section of said tubular reactor.

2. The process of claim 1 wherein said hydrogen is removed from the outer surface of the tubular reactor by the oxidation of hydrogen flowing through said permeable outer wall to produce water.

3. The process of claim 1 wherein said hydrogen is removed for the outer surface of said tubular wall by flowing an inert gas along the exterior surface of said tubular reactor to carry hydrogen away from the outer surface of the tubular reactor.

4. The process of claim 1 farther comprising a plurality of said tubular rectors located within the interior of a dehydrogenalion reactor vessel and arranged in a parallel relationship with one another in which at least some of said tubular reactors are spaced transversely from one another and spaced from the interior surface of the wall of the reaction vessel.

5. The process of claim 4 further comprising supplying an oxidizing gas into said reactor vessel and flowing said gas through said reactor vessel to react with and oxidize hydrogen flowing through hydrogen permeable outer walls of said tubular reactors.

6. The process of claim 4 further comprising supplying an inert stripping gas into said reactor vessel and flowing said inert gas within said reactor vessel along the exterior surfaces of said tubular reactors to carry hydrogen away from the outer surfaces of said tubular reactors.

7. The process of claim 1 wherein at least a portion of said spiral flow path contains a particulate dehydrogenation catalyst.

8. The process of claim 1 wherein said feedstock comprising ethyl benzene and said vinyl aromatic compound comprises styrene.

9. The process of claim 1 wherein said feedstock comprises ethyl naphthalene add the vinyl aromatic compound comprises vinyl naphthalene.

10. The process of claim 1 wherein said feedstock comprises n-propyl benzene and said vinyl aromatic compound comprises beta methylstyrene.

11. The process of claim 1 wherein said feedstock comprises cumene and said vinyl aromatic compound comprises alpha methylstyrene.

12. The process of claim 1 wherein said feedstock comprises ethyl toluene and said vinyl aromatic product comprises vinyl toluene.

13. The process of claim 1 wherein said feedstock comprises diethylbenzene and said product comprises divinylbenzene.

14. The process of claim 13 wherein said feedstock comprises a mixture of meta diethylbenzene with ortho diethylbenznne in the amount of no more than 5 mole percent.

15. A process for the production of a vinyl aromatic compound by the catalytic dehydrogenation of a $C_2$ or $C_3$ alkyl aromatic compound comprising:
(a) supplying a feedstock containing a $C_2$ or $_3$ alkyl aromatic compound and steam into a plurality of elongated tubular reactors, each characterized by to hydrogen permeable outer wall, located within the interior of a dehydrogenation reactor vessel and arranged in a parallel relationship with respect to one another in which at least some of the tubular reactors are spaced from one another and spaced linen the interior wall of the reaction vessel;
(b) heating the interior of said reaction vessel to provide heat externally of said tubular reactor to provide an amount of heat which varies along the lengths of the tubular reactors;
(c) within said tubular reactors, supplying said mixed steam and said alkyl aromatic compound into contact with a particulate dehydrogenation catalyst in said tubular reactors under temperature conditions effective to cause the dehydrogenation of said alkyl aromatic compound to a corresponding vinyl aromatic compound with the attendant production of hydrogen in the presence of said dehydrogenation catalyst;
(d) flowing said feedstock within at least a portion of said reactors along spiral flow paths extending longitudinally of said reactors and providing for an outwardly radial flow of hydrogen to provide a pressure gradient through said hydrogen permeable outer walls with the attendant flow of hydrogen through said permeable outer walls;
(e) removing hydrogen from the vicinity of the outer walls of said tubular reactors to enhance the flow of hydrogen through said hydrogen permeable outer wall from the interior to the exterior of said reactor; and
(f) recovering raid vinyl aromatic product from said tubular reactors through outlets of said tubular reactors.

16. The process of claim 15 wherein said hydrogen is removed from the outer surfaces of the tubular reactors by the oxidation of hydrogen flowing through the hydrogen permeable outer walls to produce water.

17. The process of claim 16 further comprising supplying an oxidizing gas into mid reactor vessel and flowing said gas through said reactor vessel to react with and oxidize hydrogen flowing through hydrogen permeable outer walls of said tubular reactors.

18. The process of claim 15 further comprising supplying an inert stripping gas into said reactor vessel and flowing said inert gas within said reactor vessel along the exterior surfaces of said tubular reactors to carry hydrogen away from the outer surfaces of said tubular reactors.

* * * * *